United States Patent
Boehler et al.

(10) Patent No.: US 7,079,140 B2
(45) Date of Patent: Jul. 18, 2006

(54) DIAGNOSTIC DEVICE HAVING MEANS FOR SETTING TRANSFER FUNCTIONS

(75) Inventors: Bert Boehler, Schwabach (DE); Axel Platz, Munich (DE); Claus Knapheide, Issaquah, WA (US); Bernhard Weyermann, Hoechstadt (DE)

(73) Assignee: Siemens Aktiengesellschaft, Munich (DE)

( * ) Notice: Subject to any disclaimer, the term of this patent is extended or adjusted under 35 U.S.C. 154(b) by 502 days.

(21) Appl. No.: 10/039,339

(22) Filed: Oct. 23, 2001

(65) Prior Publication Data

US 2002/0183606 A1    Dec. 5, 2002

(30) Foreign Application Priority Data

Oct. 23, 2000  (DE) ................. 100 52 540

(51) Int. Cl.
*G06T 11/20* (2006.01)
(52) U.S. Cl. ...................................... 345/440
(58) Field of Classification Search ............... 345/424, 345/440
See application file for complete search history.

(56) References Cited

U.S. PATENT DOCUMENTS 6,701,000 B1 *  3/2004  Hsieh ..................... 382/131

OTHER PUBLICATIONS

Konig et al., "Mastering Transfer Function Specification by using VolumePro Technology", Mar. 29, 2000, pp. 1-7.*
"Volume Rendering," Drebin et al., Computer Graphics, vol. 22, No. 4, Aug. 1988, United States patent practice. 65-74.
"Semi-Automatic Generation of Transfer Functions for Direct Volume Rendering," Kindlmann et al. Proc. of the Symp. On Volume Visualization '98 (1988) pp. 79-86.
"Image-Based Transfer Function Design for Data Exploration in Volume Visualization," Fang et al., Proc. of the Symp. on Vol. Visualization '98 (1998), pp. 319-326.

* cited by examiner

*Primary Examiner*—Kee M. Tung
*Assistant Examiner*—Peter-Anthony Pappas
(74) *Attorney, Agent, or Firm*—Schiff Hardin LLP

(57) ABSTRACT

A diagnostic device has a modality for generating raw data representing contents of a volume, a computer for calculating three-dimensional medical images from the raw data, an image system, an input device for setting a transfer function required for an algorithm and a display device for the medical images. The image system determines a histogram distribution of the gray-scale values, and the image system inserts user interface graphics into the displayed image which shows the histogram distribution of the gray-scale values in a histogram window and symbolically represents a trapezoidal transfer function on which values characterizing input fields for transfer functions are arranged at the associated points. A transfer function is on the basis of entries in the input fields and the selected transfer function is inserted in the histogram distribution of the gray-scale values.

6 Claims, 3 Drawing Sheets

DIAGNOSTIC DEVICE HAVING MEANS FOR SETTING TRANSFER FUNCTIONS

BACKGROUND OF THE INVENTION

1. Field of the Invention

The present invention relates to a diagnostic device of the type having a modality for generating raw data representing contents of a volume, a computer for calculating three-dimensional (3D) medical images from the raw data, an image system, an input device for setting a transfer function required for an algorithm, and a display device for the medical images.

2. Description of the Prior Art

The volume rendering algorithm is gaining increasing importance in the visualization of three-dimensional (3D) volumetric data records in medical technology in the case of computed tomography (CT) and magnetic resonance tomography (MR) and angiography examinations such as CTA or MRA.

The technique of volume rendering is used to reproduce the anatomical spatial relationship between various organs, in order to enhance insight into hidden structures, in particular of blood vessels. Different objects of the same volume such as, for example, blood vessels, bones, skin and soft parts, can be inspected simultaneously. This differentiation is calculated on the basis of a selected object threshold and characterizes the transparency, shading or color.

In the case of a non-pre-segmented volumetric data record, however, this very powerful algorithm requires the definition of a transfer function which allocates each gray-scale value an RGBA value which characterizes a transparency (A) and a color consisting of a mixture of red (R), green (G) and blue (B). The task of the transfer function is to locate and delimit anatomically coherent gray-scale value ranges. It is difficult in this process to locate the boundaries of the gray-scale value ranges, since this process is accomplished by purely empirical approaches such as are described in G. Kindlmann et al. "Semi-Automatic Generation of Transfer Functions for Direct Volume Rendering" in Proceedings Symposium on Volume Visualization '98, pages 79–86, 1998, or S. Fang et al. "Image-Based Transfer Function Design for Data Exploration in Volume Visualization" in Proceedings Symposium on Volume Visualization '98, pages 319–326, 1998. Thus, the majority of current graphical user interfaces offer only the option of defining the transfer function by means of freehand function curves (see FIG. 2) or with the aid of block or trapezoidal functions (see FIG. 3 herein) (compare also R. A. Drebin et al. "Volume Rendering" in Computer Graphics 24(4), pages 65–75, 1988). The basis for this is mostly the gray-scale value histogram or specific prior knowledge of gray-scale value ranges (for example Houndsfield units in the case of CT). Such setting options of the transfer function are complicated and inaccurate, and so it is possible to find the correct transfer function only with difficulty and a disproportionately large time outlay. This means that volume rendering is accepted only with difficulty in the clinical routine among medical practitioners.

German OS 199 55 690 discloses a three-dimensional image system which has a display with segmented elements and a view selector which permits identification of special features. The selection of the volumetric elements is made on the basis of a comparison with defined threshold values corresponding to the opacity.

SUMMARY OF THE INVENTION

An object of the present invention is to design a diagnostic device of the type initially described which permits simple setting of transfer functions for reproducing coherent gray-scale value ranges.

The object is achieved according to the invention in a diagnostic device wherein the image system has a unit for determining a histogram distribution of the gray-scale values, that the image system inserts, in the image on the display device, a user interface which shows the histogram distribution of the gray-scale values in a histogram window and symbolically represents a trapezoidal transfer function on which values characterizing input fields for transfer functions are arranged at the associated points. The transfer functions are inserted on the basis of the inputs in the histogram distribution of the gray-scale values. As a result, a quick and accurate setting of the transfer functions can be achieved in a simple way, monitoring being rendered possible by the overview in the histogram window.

It has proved to be advantageous when a selection bar is provided by means of which a number of transfer functions can be selected for setting, and activated for representation.

A precise setting can be performed when the corner points of the transfer function, and thus their gray-scale range as well as the transparency, the brightness and/or the color of the transfer function can be set and varied by means of the values in the input fields.

A good overview is retained as to which transfer function can currently be changed when the selected transfer function is marked in the histogram window.

Zooming in the histogram window can be achieved when the gray-scale value range displayed in the histogram window can be varied by means of a scroll bar.

The transfer functions can be used for the volume rendering algorithm.

The transfer functions can be used for a number of examinations when the image system has a memory for transfer functions.

It has proved to be advantageous when the image system is designed in such a way that the active transfer function is marked at its variable points in the histogram window.

DESCRIPTION OF THE PREFERRED EMBODIMENTS

Figure 1:
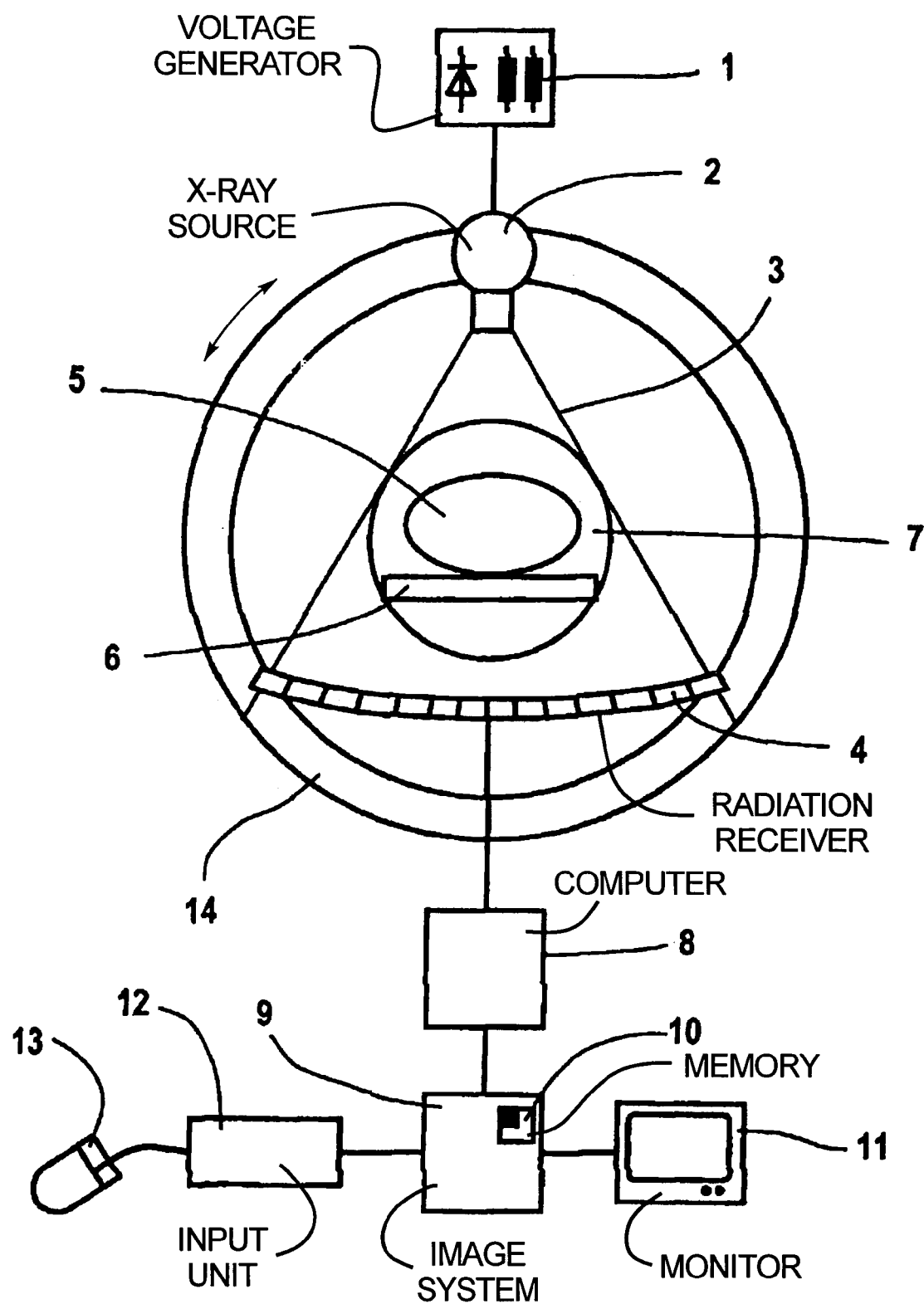
FIG. 1 is a schematic illustration of a computed tomography constructed and operating in accordance with the present invention.
Figure 2:
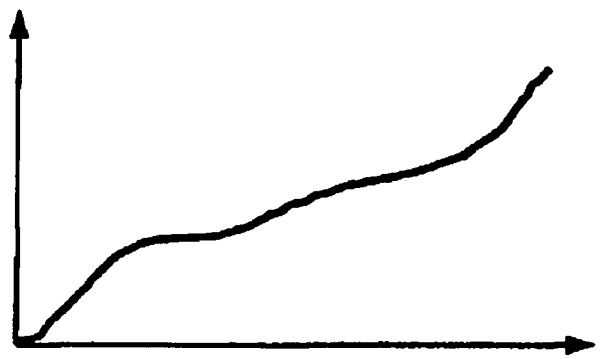
FIG. 2 shows freehand function curves as a transfer function.
Figure 3:
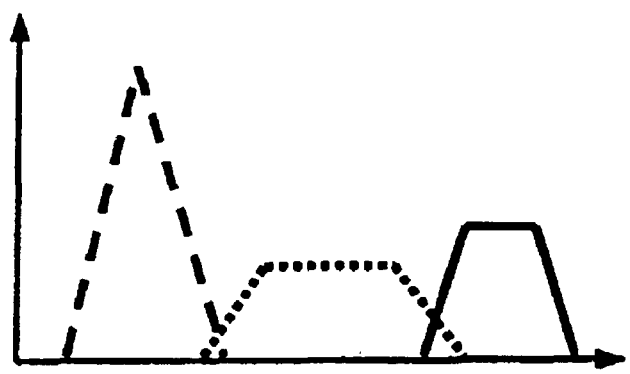
FIG. 3 shows arbitrarily settable block and trapezoidal functions as a transfer function.

The computed tomography apparatus in accordance with FIG. 1 as a modality for generating three-dimensional medical images, has a measuring unit composed of an X-ray source 2, which is fed by a voltage generator 1 and emits a fan-shaped first X-ray beam 3, and a radiation receiver 4 which is composed of a series of individual detectors, for example of 512 individual detectors. The patient 5 to be examined lies on a patient positioning table 6. In order to scan the patient 5, the measuring unit 2, 4 is rotated through 360° around a measuring volume 7 in which the patient 5 lies.

In this process, the X-ray generator 1 is operated in a pulsed fashion or with continuous radiation emission. At predetermined angular positions of the measuring unit 2, 4, sets of data are generated which are fed by the radiation receiver 4 to a computer 8 which uses the generated data records to calculate the attenuation coefficients of predetermined pixels. Connected to the computer 8 is an image system 9 which can have a transducer, a memory 10 and processing circuits. The image system 9 generates signals which are supplied to a monitor 11 for displaying the images of the radiographed layers of the patient 5. Also connected to the image system 9 is an input device 12 which has a keyboard and/or a mouse 13.

The change in the direction of the useful radiation beam 3 is performed by rotating a gantry 14 with the aid of a rotary device (not illustrated) on which the X-ray source 2 and the radiation receiver 4 are mounted.

By constructing a number of layers, or in a spiral mode, this computed tomography apparatus can generate 3D volumetric data records which can be further processed by volume rendering for the purpose of better visualization in the image system 9. In this process, it is possible to use the above-described algorithms of pattern recognition which offer the possibility of determining the boundaries, which are difficult to locate, of the gray-scale value ranges and their gradients.

The purpose of simple delimitation of coherent gray-scale value ranges and setting the transfer functions is served by the device according to the invention, which employs a user-friendly graphical interface.

Figure 4:
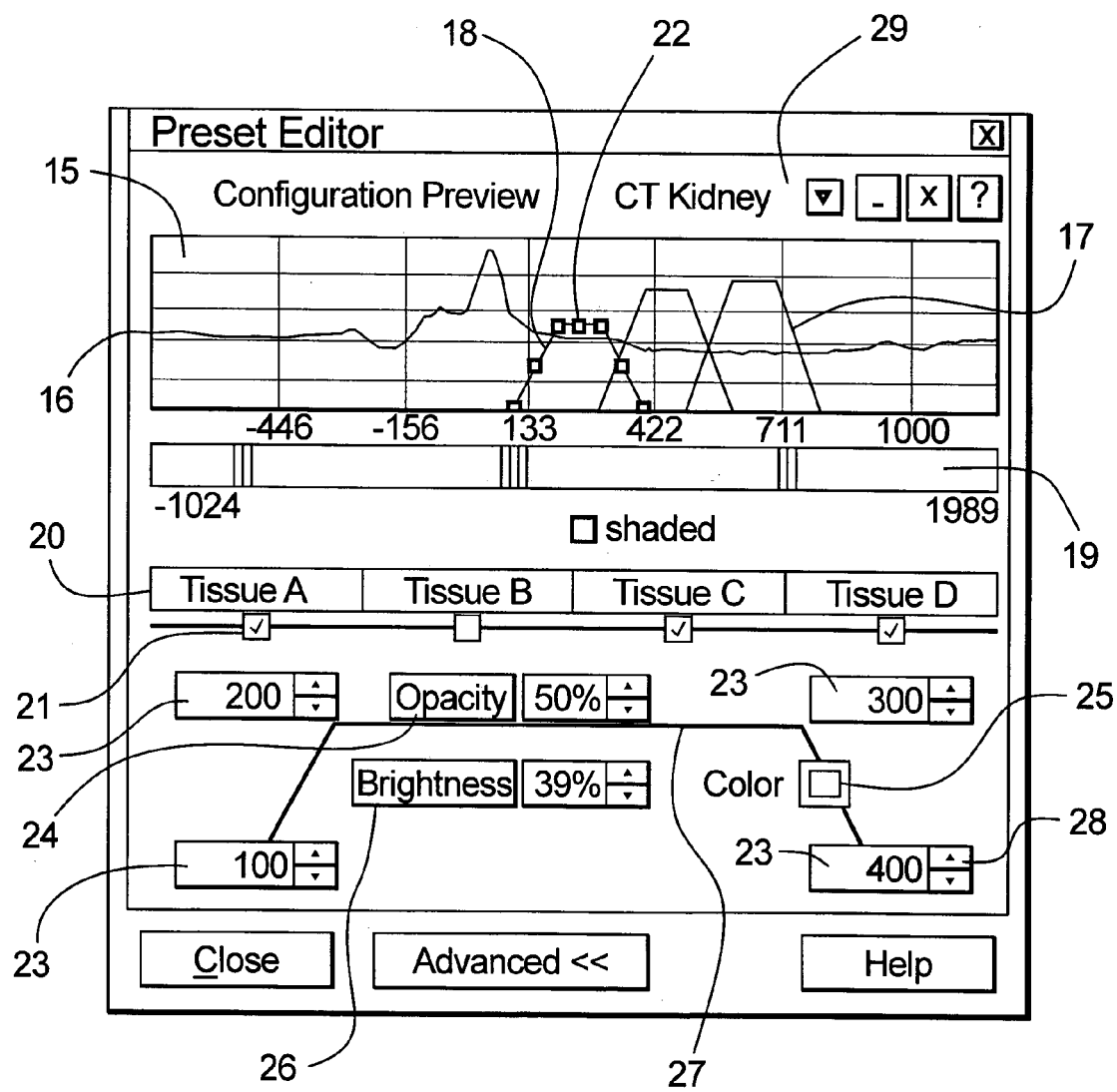
FIG. 4 shows a graphical user interface for setting the transfer functions in accordance with the invention.

The values of the transfer functions can easily be identified by means of this graphical user interface illustrated in FIG. 4. The user interface has a histogram window 15 in which the histogram distribution 16 of the gray-scale values is displayed. Activated transfer functions 17 and 18 are inserted in the histogram window 15.

Reproduced below the histogram window 15 is a scroll bar 19 by means of which the size and position of the illustrated range can be selected from the overall range.

A selection bar 20 can be used to select the transfer functions 17 and 18, it being possible to activate a number of transfer functions 17 and 18 by means of check boxes 21. The transfer function 18, of which the settings are about to be changed, is highlighted in color in the selection bar 20. At the same time, the corresponding associated transfer function 18 is marked in the histogram window 15, for example by small boxes 22. These markings correspond to input fields 23 to 26, which are arranged next to a symbolically represented trapezoidal function 27.

The input fields 23 at the corner points of the trapezoidal function at which the gray-scale values of these corner points are entered can be used to set their form with point accuracy, i.e., the steepness of the edges in the transfer function and the bounds of the ranges, which changes in the histogram window 15 in accordance with the settings. The transparency (opacity), and thus the level of the transfer function, can be varied by means of the input fields 24 on the straight line.

All the inputs can be entered in a known way by inputting the desired numerical values or by varying the numerical values by means of the increment or decrement buttons 28. In addition, it is possible in the input field 25 to select the color on the descending straight line, and in the input field 26 to select the brightness of the transfer function and the gray-scale value range marked by the transfer function. This color is also then adopted by the selected transfer function 18 and the marking below the selection bar 20.

Transfer functions stored in the memory 10 can be called up in the header bar via a pull-down menu 29.

Transfer functions 17 and 18 can be selected and set clearly and simply by means of the diagnostic device according to the invention. The active transfer functions 17 and the selected transfer function 18 can be recognized distinctly. The desired setting values can be entered quickly and easily, and immediate feedback about their effects is obtained. The illustrated gray-scale value range can be enlarged and zoomed in on using the scroll bar 19. It is possible to employ on stored transfer functions which can also be adapted to the desired curves.

Although modifications and changes may be suggested by those skilled in the art, it is the intention of the inventors to embody within the patent warranted hereon all changes and modifications as reasonably and properly come within the scope of their contribution to the art.

We claim:

1. A diagnostic device comprising:
an arrangement for generating raw data representing contents of a volume;
a computer connected to said arrangement for calculating gray-scale values, representing a three-dimensional image of said volume contents, from said raw data;
an image system connected to said computer for generating image signals, according to an algorithm employing an algorithmic trapezoidal transfer function which assigns at least one optical property to the respective gray-scale values, from said gray-scale values;
a monitor connected to said image system and supplied with said image signals for displaying said three-dimensional image;
a user-operable input unit connected to said image system;
said image system generating a histogram distribution of said gray-scale values and displaying user interface graphics on said monitor including a histogram window in which said histogram distribution is displayed, said image system in said graphics also displaying a symbolic trapezoidal transfer function with a plurality of input fields respectively associated with different points of said symbolic trapezoidal transfer function, said input unit allowing entries into said input fields to set the algorithmic trapezoidal transfer function employed in said algorithm, and said image system inserting a representation of the algorithmic trapezoidal transfer function in said histogram window; and
said image system displays a selection bar in said graphics and representing all of said plurality of algorithmic trapezoidal transfer functions, which are selectable via said selection bar, in said histogram window, and said input unit allowing one of a plurality of algorithmic transfer functions identified by said selection bar to be selected for representation in said graphics, and said image system marking the set algorithmic trapezoidal transfer function at said points of said symbolic trapezoidal transfer function.

2. A diagnostic device as claimed in claim 1 wherein said symbolic trapezoidal transfer function has corner points, and wherein said input fields are respectively associated with said corner points and wherein said input unit allows, by respective entries in said input fields, selection of said corner points and thus selection of their respective gray-scale range.

3. A diagnostic device as claimed in claim 1 wherein said at least one optical property is selected from the group consisting of brightness, color and transparency, and wherein said image system displays an input field in said graphics allowing said at least one optical property to be varied via said input unit.

4. A diagnostic device as claimed in claim 1 wherein said histogram distribution displayed in said histogram window has a gray-scale value range, and wherein said image system displays a scroll bar in said graphics allowing, via said input unit, variation of said gray-scale range.

5. A diagnostic device as claimed in claim 1 wherein said image system generates said image signals according to a volume rendering algorithm.

6. A diagnostic device as claimed in claim 1 wherein said image system comprises a memory in which a plurality of different algorithmic trapezoidal transfer functions are stored, and wherein said image system displays an input field in said graphics allowing selection, via said input unit, of one of the algorithmic trapezoidal transfer functions stored in said memory for use as said algorithmic trapezoidal transfer function employed in said algorithm.

* * * * *